(12) United States Patent
Radulescu

(10) Patent No.: US 6,660,830 B1
(45) Date of Patent: Dec. 9, 2003

(54) PEPTIDES WITH ANTIPROLIFERATIVE PROPERTIES

(76) Inventor: Razvan T Radulescu, Guardinistrasse 47, München D-81375 (DE)

(*) Notice: Subject to any disclaimer, the term of this patent is extended or adjusted under 35 U.S.C. 154(b) by 0 days.

(21) Appl. No.: 09/155,165
(22) PCT Filed: Mar. 26, 1997
(86) PCT No.: PCT/DE97/00643
§ 371 (c)(1), (2), (4) Date: Jun. 7, 1999
(87) PCT Pub. No.: WO97/35873
PCT Pub. Date: Oct. 2, 1997

(30) Foreign Application Priority Data

Mar. 26, 1996 (DE) .......................................... 196 11 939
Dec. 20, 1996 (DE) .......................................... 196 53 445

(51) Int. Cl.[7] ................................................ C07K 5/00
(52) U.S. Cl. ......................... 530/300; 530/303; 514/2; 514/3
(58) Field of Search ................... 514/2, 12, 3; 530/303, 530/324, 300

(56) References Cited

U.S. PATENT DOCUMENTS 5,573,925 A * 11/1996 Halazonetis
5,851,991 A * 12/1998 Lee et al.

FOREIGN PATENT DOCUMENTS

EP 0685493 A1 * 12/1995
WO WO 94/04696 * 3/1994

OTHER PUBLICATIONS

Radulescu et al., BBRC 206:97–102.*
Jian, Sci. Amer. 271:58, 1994.*
Chatterjee et al, Cancer Immunol Immunother 38:75–82, 1994.*
Gura, Science 278:1041, 1997.*
Buckbinder et al, Nature 377:646–649, 1995.*

* cited by examiner

Primary Examiner—Larry R Helms
(74) Attorney, Agent, or Firm—Nixon Peabody LLP

(57) ABSTRACT

The present invention relates to antiproliferative peptides which are derived from a tumor suppressor protein and bind to growth factor segments or growth factor receptor segments. The invention also relates to nucleic acids (DNAs/RNAs) which code for these peptides and structurally homologous peptide nucleic acids and pharmaceutical compositions containing such peptides. The invention can be used in biotechnology, molecular biology, bioinformatics and in the diagnosis and therapy of hyperproliferative disorders, in particular cancer and atherosclerosis.

14 Claims, 15 Drawing Sheets

PEPTIDES WITH ANTIPROLIFERATIVE PROPERTIES

The present invention pertains to peptides having antiproliferative properties, nucleic acids (DNA/RNA) coding for said peptides, peptide nucleic acids that are structurally homologous to said nucleic acids and the use of said peptides, said nucleic acids, said peptide nucleic acids and/or pharmaceutical compositions thereof in biotechnology, in molecular biology, bioinformatics, as well as the diagnosis and therapy of hyperproliferative diseases, particularly cancer and atherosclerosis.

In oncology there are a variety of different treatment regimens primarily based on surgical procedures, chemotherapy or radiation therapy. However, these methods have not provided the desired results in cancer therapy. According to current statistics in the United States of America every third person living there develops cancer and every fifth person is going to die therefrom. This number is likely to apply to all industrialized nations all over the world and has not significantly changed for more than a decade. Moreover, it is to be noted that the efficacy of treating cancer has not substantially improved during the past twenty years since the five-year survival rate has essentially stayed the same for most cancer types (R. N. Proctor "The Sciences", March/April 1995, pp. 20–24).

Therefore, the objective of the present invention is to provide a means to inhibit the growth of a variety of different types of cancer eventually resulting in a regression of the tumors.

This objective is achieved by a peptide by a nucleic acid (DNA/RNA), by a peptide nucleic acid, by a pharmaceutical composition and by the use of said peptides, by the use of the DNA/RNA, by the use of the peptide nucleic acid and by the use of a pharmaceutical composition the present invention. Preferred embodiments are illustrated in the dependent claims.

The present inventor has found a promising approach in the treatment of cancer which is to utilize specific peptides that block substances causing cancer, particularly oncogenic proteins. The peptides of the present invention are characterized by a short sequence length which renders them economical in terms of their synthesis. Moreover, they are able to efficiently penetrate cells and, as a result, are capable of neutralizing intracellular proteins that promote the development of cancer.

It has previously been found that in a variety of cancer types tumor suppressor genes are deleted or mutated which in turn results in an insufficient provision of the corresponding gene products. This finally leads to the development of cancer (A. G. Knudson, Proc. Natl. Acad. Sci., USA (1993), vol.90, pp 10914–10921; A. J. Levine, Sci. Am. "Science & Medicine", Jan./Feb. 1995, pp.28–37).

Defects in tumor suppressor proteins, such as RB1, also seem to be important for the pathogenesis of other hyperproliferative diseases, e.g. atherosclerosis. The present inventor has found that it is sufficient to introduce parts of a tumor suppressor protein into cells in order to block growth factors that accelerate the uncontrolled growth of cells. It is not possible to introduce the entire tumor suppressor protein since such a protein is too long and is in most cases is subject to proteolytic degradation, thus preventing the protein from exerting its effect. On the other hand, if only parts of tumor suppressor proteins are utilized, said parts are too rapidly degraded as well, i.e. they are not sufficiently stable.

The peptides according to the present invention are therefore synthetic fusion poly-peptides consisting of the components (A) and (B), wherein these components are connected to each other as AB or BA. The first component (A) comprises an effective part of a tumor suppressor protein—in such a form as first found by the inventor—or is hydropathically homologous thereto. The second component (B) comprises a sequence that stabilizes the first component (A). According to the invention the peptide of the present invention binds to a growth factor or a growth factor receptor, preferably to the sequence LXCXE (SEQ. ID. NO: 1) therein, more preferably to the LXCXE (SEQ. ID. NO: 1) sequence in insulin, i.e. to LVCGE (SEQ. ID. NO: 2) (Radulescu et al., Biochemical and Biophysical Research Communications 1995, vol. 206, pp. 97–102). Since the growth factors IGF-1 and IGF-2 comprise the sequence FVCGD (SEQ. ID. NO: 3), which sequence is hydropathically homologous to the segment LVCGE (SEQ. ID. No: 2) in insulin (R. Radulescu & C. Wendtner, J. Mol. Recognition 1992, vol. 5, pp. 133–137) the peptide of the invention binds to IGF-1 and IGF-2 as well.

The term "hydropathically homologous" is used herein according to the teaching of Kyte and Doolittle (J. Kyte & R. F. Doolittle, J. Mol. Biol. 1982, vol. 157, pp. 105–132) and J. E. Blalock and Smith, E. M. (Biochemical and Biophysical Research Communications, Vol. 121, no. 1, pp. 203–207 (1984)).

The component (A) is further characterized by the fact that it is hydropathically complementary to a fragment of a growth factor or of a growth factor receptor according to the complementary peptide theory (J. E. Blalock, Trends in Biotechnology, vol. 8, pp. 140–144, June 1990) or according to the three-dimensional configuration, respectively. Examples for growth factors are: insulin, IGF-1, IGF-2, EGF, FGF, angiogenin, NGF and PDGF.

According to the present invention the effective regions for component (A) of the peptide according to the present invention may be derived from the following tumor suppressor gene products: RB1, P107, P130, WT1, TP53, NF1, NF2, VHL, APC, NB1, MLM, MEN1, BCNS, RCC, BRCA1, BRCA2, DCC, MTS1=p16, MTS 2, p21, p27 and others. In a preferred embodiment, the component (AN comprises a section of RB1, in particular amino acids 649–654 of RB1, i.e. LFYKKV (SEQ. ID. No: 4) or is hydropathically homologous thereto.

The component (B) of the fusion peptide has the property of stabilizing said component (A) as a cofactor so that the latter is not proteolytically degraded in the cell. This may be achieved by the peptides of the present invention rapidly arriving at the cell nucleus where they are less prone to proteolytic degradation (R. Fahraeus et al., Current Biology 1996, vol.6, no. 1, pp. 84–91) or by using branched components (B) such as polylysine branches or polylysine cores or by using D-amino acids. In a preferred embodiment, the component (B) is a polylysine core (R. Radulescu et al., Biochemical and Biophysical Research Communications, 1995, vol. 206, pp. 97–102; and G. Fassina, EPO 0 481 930 A2) or a nuclear localization sequence (NLS), particularly a SV40 NLS or Penetratin or a bipartite NLS or the RNP A1 NLS (M9 region). For the construction of peptides which are preferably directed to the cell nucleus general reference is made to Sheldon et al., Proc. Natl. Acad. Sci. USA, vol. 92, pp. 2056–2060 (1995); Dingwall et al., Trends in Biochemical Sciences 16, pp. 478–481 (1991), M. S. Moore, Current Biology, vol. 6, no. 2, pp. 137–140 (1996); D. A. Jans, FASEB Journal, 1994, vol 8, pp. 841–847; J. Moroianu & J. F. Riordan PNAS, 1994, vol. 91, pp. 1677–1681 and D.Derossi et al., Journal of Biological Chemistry, 1994, vol. 269, pp. 10444–10450.

In a preferred embodiment, the component (A) has the following sequence or is homologous thereto in at least two positions:

NH$_2$-LFYKKV-COOH (P1) (SEQ. ID. No: 4)

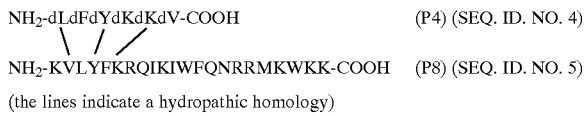

NH$_2$-dLdFdYdKdKdV-COOH (P4) (SEQ. ID. NO. 4)

NH$_2$-KVLYFKRQIKIWFQNRRMKWKK-COOH (P8) (SEQ. ID. NO. 5)

(the lines indicate a hydropathic homology)

From the above the following preferred peptides according to the present invention may be derived:

NH$_2$-[LFYKKVGGG]$_4$-[KRG]$_2$-KG-COOH (P2) (SEQ. ID. No: 6)

This peptide is a combination of the sequence P1 and the polylysine core [GGG]$_4$-[KRG]$_2$KG (SEQ. ID. No: 7)

NH$_2$-[LFYKKVGGG]$_4$-[K]$_2$-KG-COOH (P2i) (SEQ. ID. No: 8)

This peptide is a combination of the sequence P1 and the polylysine core [GGG]$_4$-[K]$_2$-KG (SEQ. ID. No: 9).

NH$_2$-[dLdFdYdKdKdV-GGG]$_4$-[1KdRG]$_2$-1KG-COOH (P3) (SEQ. ID. No: 6)

This peptide is a combination of the sequence P4 and the polylysin core [GGG]$_4$-[1KdRG]$_2$-1KG (SEQ. ID. No: 7).

NH$_2$-[dLdFdYdKdKdVGGG]$_4$-[1K]$_2$-1KG-COOH (P3i) (SEQ. ID. No: 8)

This peptide is a combination of the sequence P4 and the polylysine core [GGG]$_4$-[1K$_2$-1KG (SEQ. ID. No: 9).

NH$_2$-LFYKKVPKKKRKV-COOH (P5) (SEQ. ID. No: 10)

This peptide P5 is composed of the sequence P1 (SEQ. ID. No: 4 and the nuclear localization sequence of the large T antigen of the SV40 virus.

NH$_2$-LFYKKVRQIKIWFQNRRMKWKK-COOH (P6) (SEQ. ID. No: 11)

This peptide P6 is a combination of the sequence P1 (SEQ. ID. No: 4) and Penetratin, a sequence consisting of 16 amino acids located within the Antennapedia homeodomain, which sequence mediates translocation across membranes and thus also nuclear localization.

NH$_2$-[dKdVdLdYdFdKGGG]$_4$-[1KdRG]$_2$-1KG-COOH (P7s) (SEQ. ID. No: 12)

This peptide P7s is a combination of the sequence dKd-VdLdYdFdK which is hnydro-pathically homologous to P1 and the polylysine core [GGG]$_4$1KdRG]$_2$1KG (SEQ. ID. No: 7).

NH$_2$-[dKdVdLdYdFdKGGG]$_4$-[1K]$_2$-1KG-COOH (P7) (SEQ. ID. No: 14)

This peptide P7 is a combination of the sequence dKd-VdLdYdFdK (SEQ. ID. No. 13), which is hydro-pathically homologous to P1 and the polylysine core [GGG]$_4$-[1K]$_2$-1KG (SEQ. ID. No: 9).

NH$_2$-KVLYFKRQIKIWFQNRRMKWKK-COOH (P8) (SEQ. ID. No: 5)

This peptide P8 is a combination of the sequence dKd-VdLdYdFdK (SEQ. ID. No: 13) which is hydro-pathically homologous to P1 and Penetratin.

"D" and "L" specify the configuration of the amino acids that are shown in the one-letter code.

The peptides of the present invention normally comprise L- and/or D-amino acids. According to the present invention the all-L-forms, the all-D-forms, the retro-inverse isomers and the corresponding permutations of the L- and D-form of each amino acid are within the scope. Moreover, according to the present invention all permutations of the oxidized and reduced forms of each amino acid and amino acids both in the free form and bearing protective groups are within the scope. The most effective concentration of the peptides according to the present invention is in the range of from $10^{-4}$ to $10^{-5}$ M, with other effective concentrations being also possible depending on the specific application. As far as branched peptides are concerned, it has been shown to be advantageous that they are present in the all-D form. It is assumed that linear peptides containing an NLS enter the cell nucleus; branched peptides are likely to enter the cell nucleus, but they may also be effective outside the nucleus.

The peptides according to the present invention may be designated "SCAPs", i,e. "Synthetic Cofactor-associated Anti-oncogenic Peptides".

The preparation of the peptides according to the present invention is preferably performed according to the common solid-phase method (see G. A. Grant, "Synthetic Peptides", W.H. Freeman and Company, New York, 1992). The subsequent purification of the peptides according to the present invention is carried out and is verified as described ((R. Radulescu et al., Biochemical and Biophysical Research Comnmunications 1995, vol. 206, pp. 97–102). The latter reference also provides an example for using the peptides of the present invention for the biotechnological purification of growth factors, e.g. insulin, and growth factor receptors. In order to biotechnologically isolate growth factors and growth factor receptors, the peptides according to the present invention that carry an NLS could be coupled to a chromatography column comprising a heparan sulfate matrix.

The components (A) and (B) of the peptides according to the present invention may also be cleaved from the corresponding proteins and connected with each other according to standard methods. Additional techniques for the preparation of the peptides are within the ordinary skill (see G. A. Grant, "Synthetic Peptides", W.H. Freeman and Company, New York, 1992).

The invention further relates to DNA/RNA coding for the peptides according to the present invention with the DNA/RNA sequence being derived from the genetic code.

In a preferred embodiment, the following DNA/RNA sequence codes for the above mentioned amino acid sequences (P1) and (P4) that represent component (A) of the peptide according to the present invention:

5'-CUU UUC UAC AAG AAG GUU-3' (D1) (SEQ. ID. No: 15)

In a further preferred embodiment, the following DNA/RNA sequence codes for the above mentioned peptide. (P5) according to the present invention:

5'-CUU UUC UAC AAG AAG GUU CCU AAG AAG AAG CGU AAG GUU-3' (D5) (SEQ. ID. No: 16)

In a preferred embodiment, the following DNA/RNA sequence codes for the above mentioned peptide (P6) according to the present invention 5'-CUU UUC UAC AAG AAG GUU CGU CAA AUA AAG AUA UGG UUC CAA AAU CGU CGU AUG AAG UGG AAG AAG-3' (D6) (SEQ. ID. No: 17)

In a preferred embodiment, the following DNA/RNA sequence codes for the above mentioned peptide (P8):

5'-AAG GUU CUU UAC UUC AAG CGU CAA AUA AAG AUA UGG UUC CAA AAU CGU CGU AUG AAG UGG AAG AAG-3' (D8) (SEQ. ID. No: 18)

The DNA/RNA sequences coding for the peptides of the present invention may be incorporated into adequate vectors for use in the gene therapy of cancer. A survey of the methodology is to be found in R. C. Mulligan, Science 1993, vol. 260, pp. 926–932.

The above DNA/RNA sequences comprise DNA/RNA sequences hybridizing thereto under stringent conditions, as known to those skilled in the art. These are in particular DNA/RNA sequences that hybridize with the above DNA/RNA sequences at about 20° C. below the melting point of DNA/RNA. Moreover, the above mentioned DNA/RNA sequences comprise DNA/RNA sequences that are related to the above mentioned DNA/RNA sequences according to the degeneracy of the genetic code.

The present invention may also be applied in bioinformatics and molecular biology. The following strategy could be applied to identify tumor suppressor proteins that interact with a growth factor or its receptor. The cDNA of the corresponding growth factor or its receptor, respectively, could be derived from the NCBI data base and this cDNA may be translated according to the complementary peptide strategy into a complementary DNA and into a peptide by means of the DNA Strider software. For the resulting complementary peptides homologous proteins/peptides may be found (the sought tumor suppressors) by means of the BLAST algorithm in the OWL data base navigator. On the other hand, it is possible to start with the tumor suppressor cDNA and look in an analogous manner for growth factors or their receptors, respectively, as interacting partners. This method could accelerate and facilitate the cloning of (novel) tumor suppressor proteins or (novel) growth factors or growth factor receptors, respectively. By way of example, the cDNA of the human EGF precursor has been copied from the NCBI data base and copied into the DNA Strider software. By means of said software the complementary DNA sequence(s) has/have been derived from the EGF precursor cDNA and this DNA sequence(s) has/have been translated into peptides, into so-called peptides complementary to the EGF precursor protein. Subsequently, by means of the BLAST algorithm in the OWL data base navigator peptides/proteins were searched for that are homologous to these complementary peptides. As a result, several nuclear proteins were revealed to be homologous to the EGF precursor, for instance the p130 protein that is structurally and functionally related to RB1, in particular the amino acids 290–313 of p130. More specifically, if the regions are aligned in an anti-parallel fashion to each other, the amino acids of the EGF precursor 209–213 (REGSN) and the amino acids 305–309 of p130 (IGTLS) are hydropathically complementary to each other and are therefore potential binding sites in the assumed complex between the EGF precursor and p130. Thus, the amino acid sequence IGTLS or sequences that are hydropathically homologous thereto may represent component (A) of an antiproliferative peptide of the present invention.

As far as therapeutic applications are concerned, the peptides of the present invention are used in a pharmaceutical composition either alone or together with several common adjuvants, fillers and/or additives. A particularly advantageous embodiment is the combination of the above mentioned peptides P3 and P6 as well as of P3 and P5, respectively. As far as the form of administration of the pharmaceutical composition is concerned, the following is appropriate: ointments, solutions, dispersions, emulsions, aerosols, foams, particulate matter (for example granulates, agglomerates, powder, micropearls, adsorbates), pills, pastilles, tablets, dragées or capsules. The peptides of the present invention may also be used together with cytostatic remedies or in combination with radiation treatments. The peptides are preferably administered locally, intracutaneously or transcutaneously, for systemic administration preferably intravenously, intraarterially, orally and rectally. The administration into cavities is preferably carried out intrathecally, intraperitoneally or intracavitarily.

The peptides, DNA/RNA sequences and pharmaceutical compositions according to the present invention are useful as drugs for treating cancer and are applied according to the present invention in this manner, displaying a marked cytotoxic effect.

A particular effectiveness is seen against breast cancer cells, osteosarcoma cells and leukemia cells. Due to the underlying concept, the peptide according to the present invention generally acts on all tumor cells that display a defective retinoblastoma gene or protein, respectively.

The invention will be described with reference to the 15 figures and to tables, wherein.

Table 1 shows the P5- and P6-mediated inhibition of the cell cycle progression in MCF-7 cells which, by contrast, is not achieved with Penetratin;

Table 2 shows the P5- and P6-mediated inhibition of the cell cycle progression in SAOS-2 cells which, by contrast, is not achieved with Penetratin.

Figure 1:
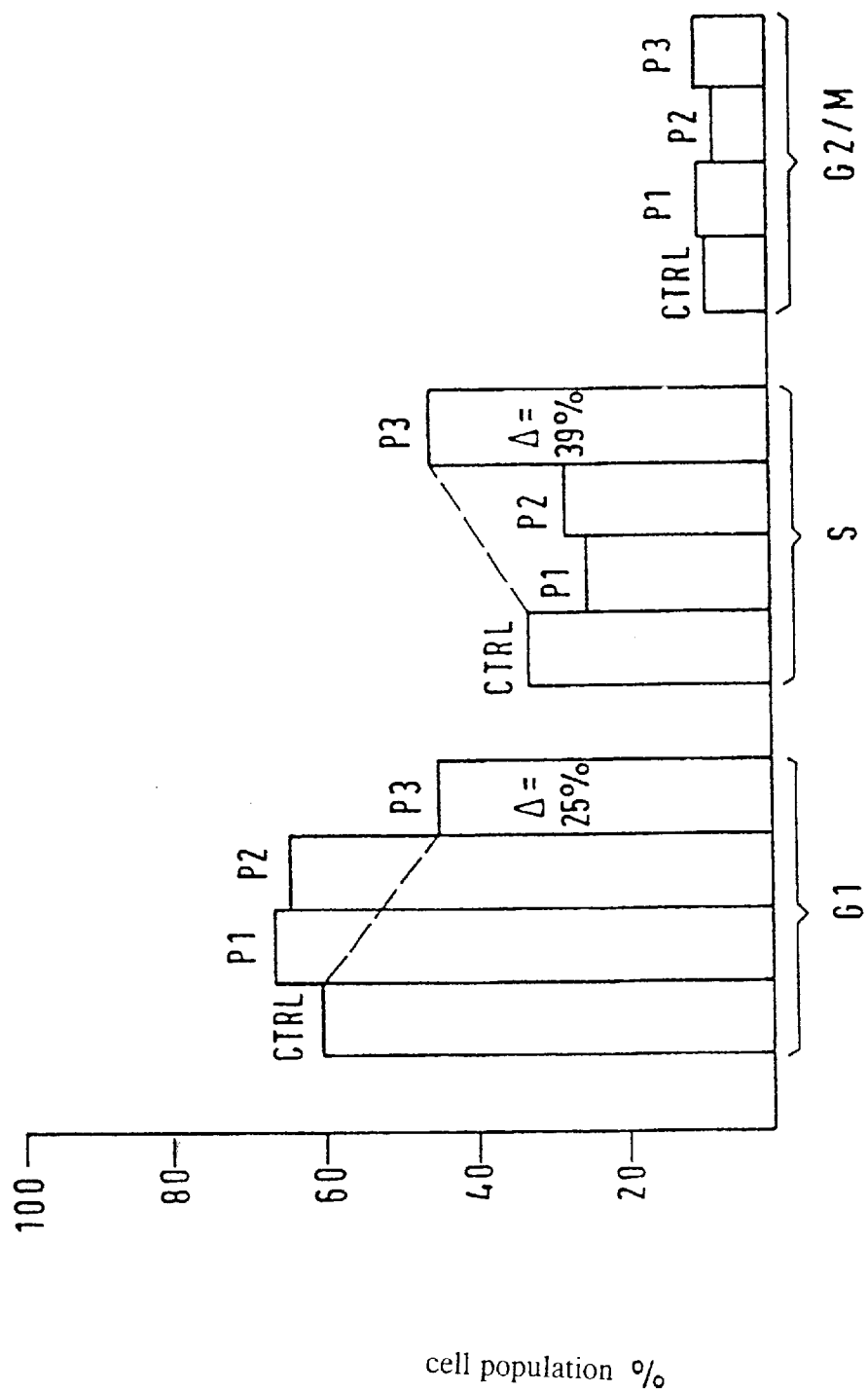
FIG. 1 to FIG. 12 shows the % cell population of MCF-7 cells or SAOS-2 cells in the G1-, S- and G2/M phase in the presence or absence of different peptides of the present invention.

FIG. 1 shows that, under serum-free conditions, the peptide P3 of the present invention at a concentration of $10^{-5}$ M reduces the G1 phase and increases the S phase in MCF-7 cells that have been synchronized in the G0/G1 phase. The morphology of the cells treated with P3 corresponds to that of apoptotic cells.

Figure 2:
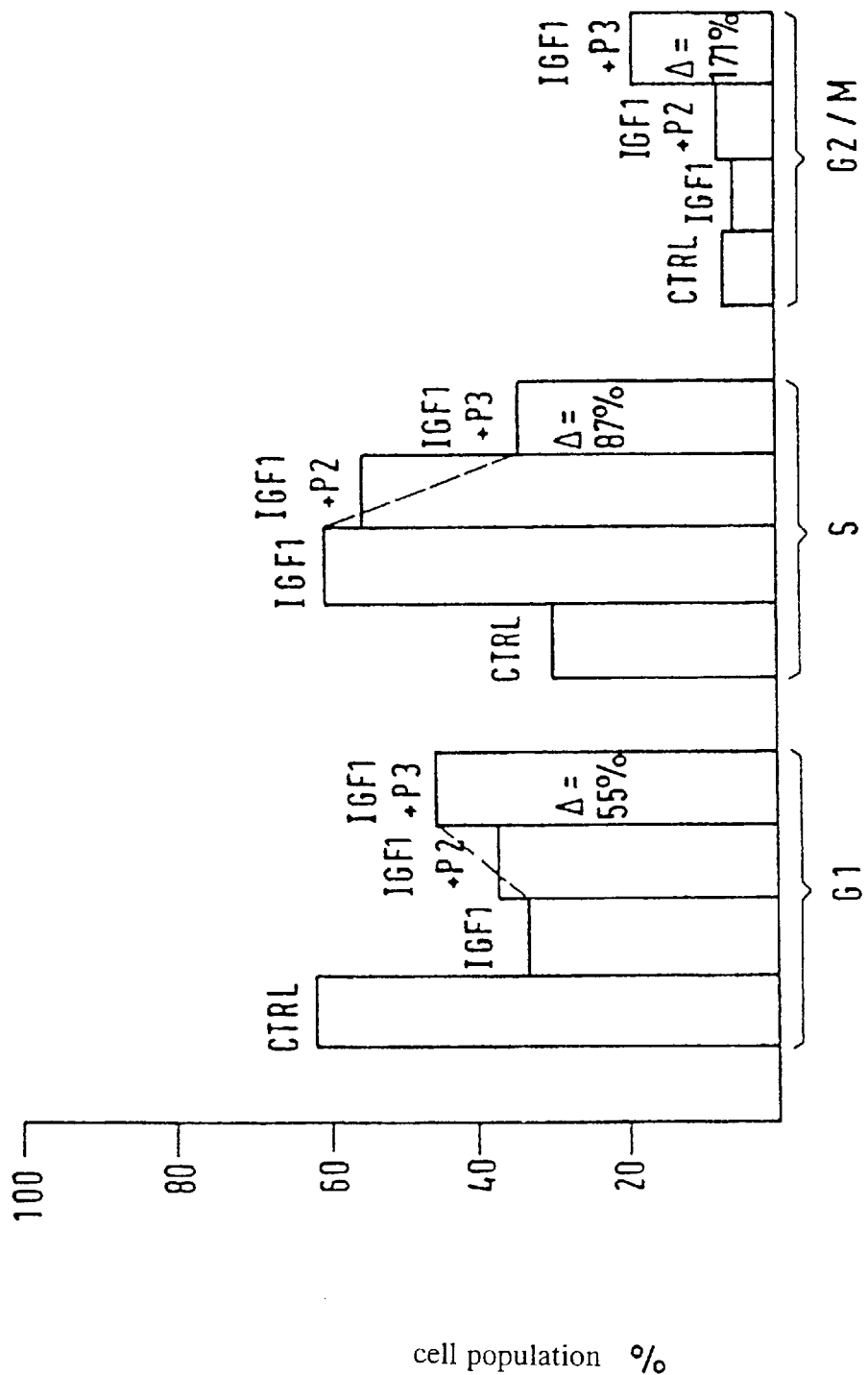

FIG. 2 shows that the peptide P3 of the present invention at a concentration of $10^{-5}$ M results in an increase of the G1 and G2/M phases as well as in a decrease of the S phase in MCF-7 cells that have been stimulated by insulin-like growth factor 1 (IGF-1) at an optimal concentration of $10^{-8}$ M. Accordingly, P3 blocks the effect of IGF-1 on MCF-7 cells. In particular, P3 delays the progression of the cell cycle caused by IGF-1 and thus delays cell division. The morphology of the cells treated with P3 corresponds to that of apoptotic cells.

Figure 3:
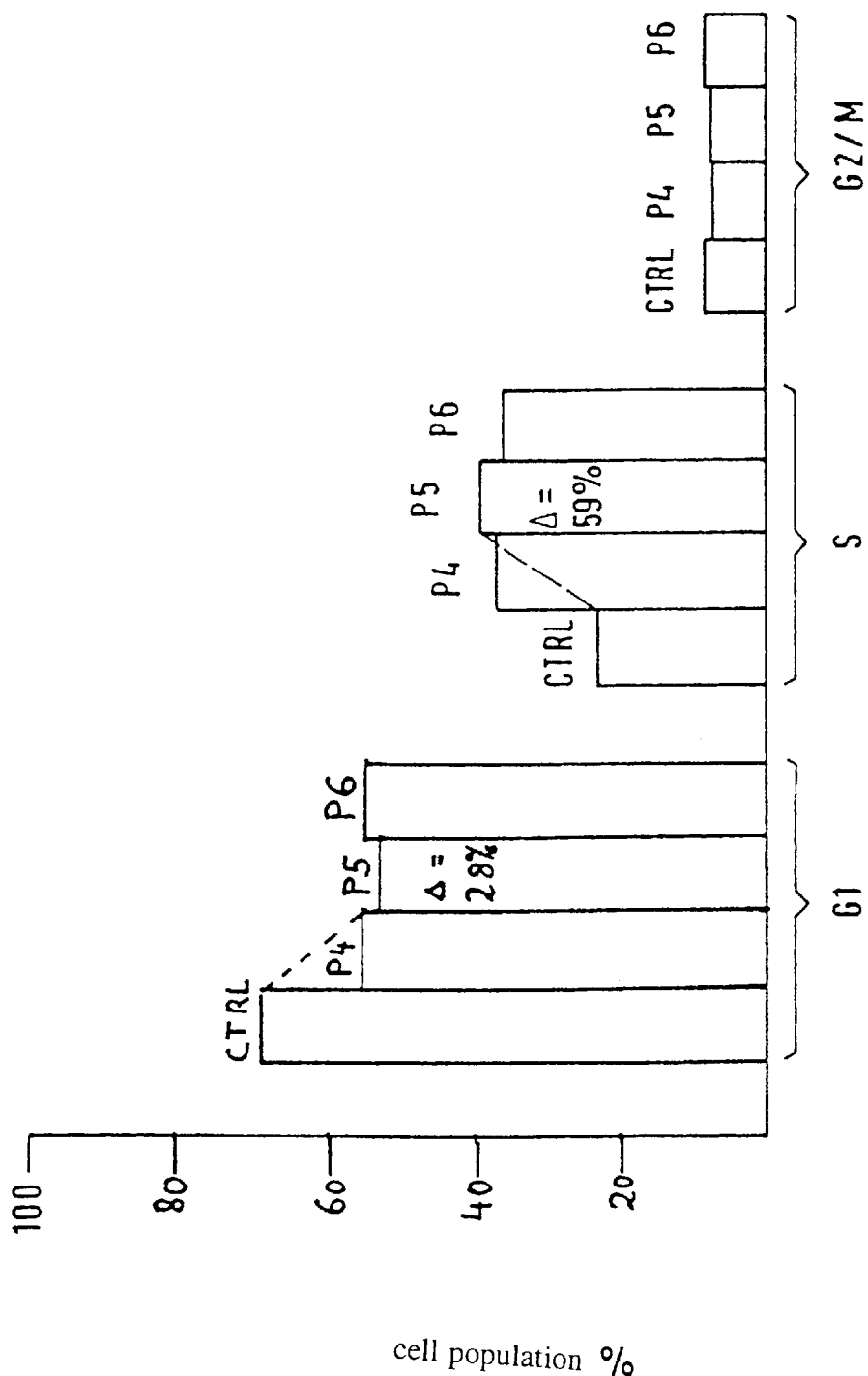

FIG. 3 shows that, under serum-free conditions, each of the peptides P4, P5 and P6 at a concentration of $10^{-5}$ M reduces the G1 phase and increases the S phase in MCF-7 cells that have been synchronized in the G0/G1 phase. The morphology of said cells, in particular of those treated with P6, corresponds to that of apoptotic cells.

Figure 4:
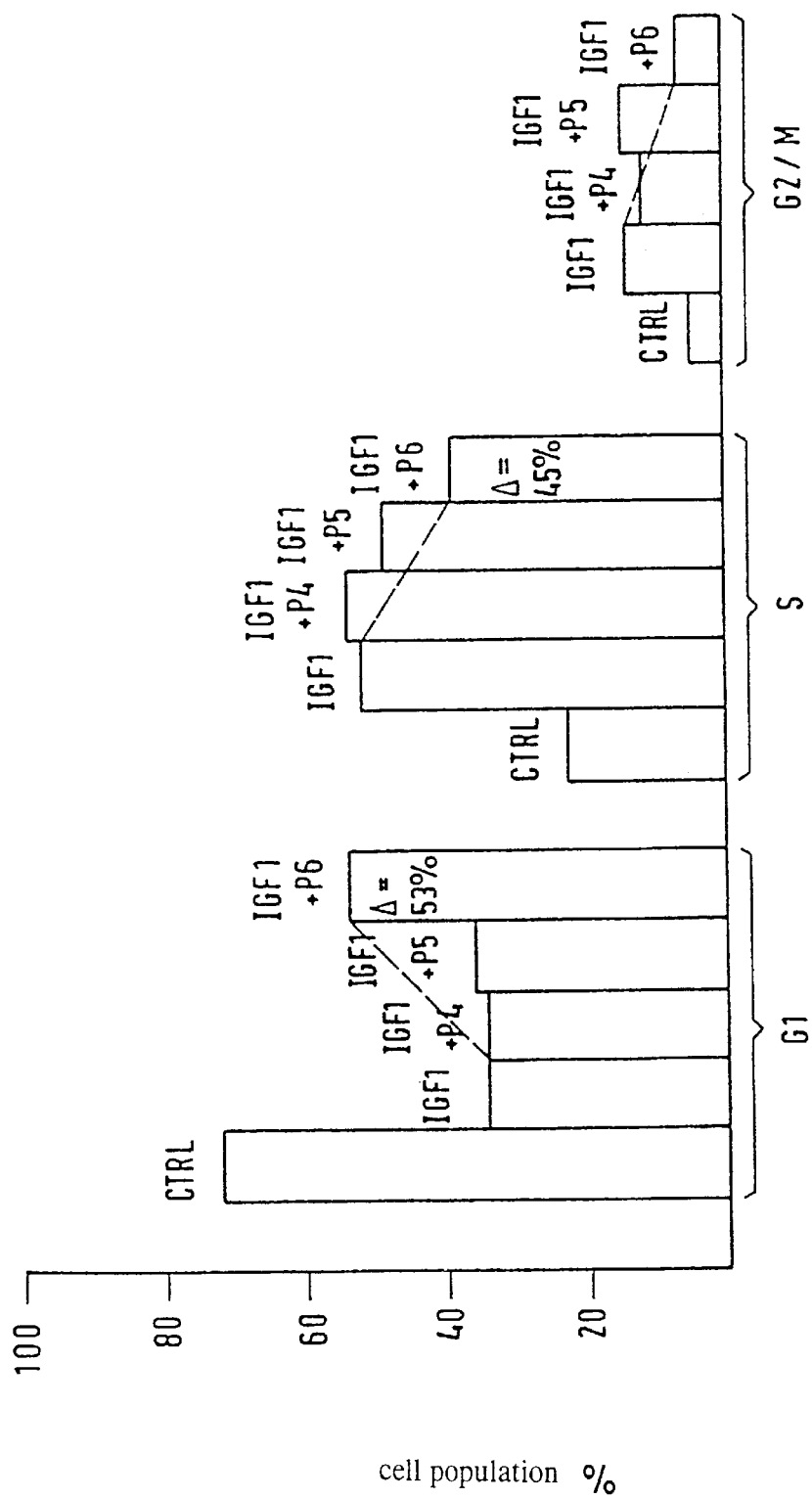

FIG. 4 shows that the peptide P6 of the present invention at a concentration of $10^{-5}$ M increases the G1 phase as well as decreases the S phase in MCF-7 cells that have been stimulated with IGF-1 at an optimal concentration of $10^{-8}$ M. Therefore, P6 blocks the effect of IGF-1 on MCF-7 cells. In particular, P6 delays the progression of the cell cycle caused by IGF-1 and thus delays cell division. The morphology of the cells treated with P6 corresponds to that of apoptotic cells.

Figure 5:
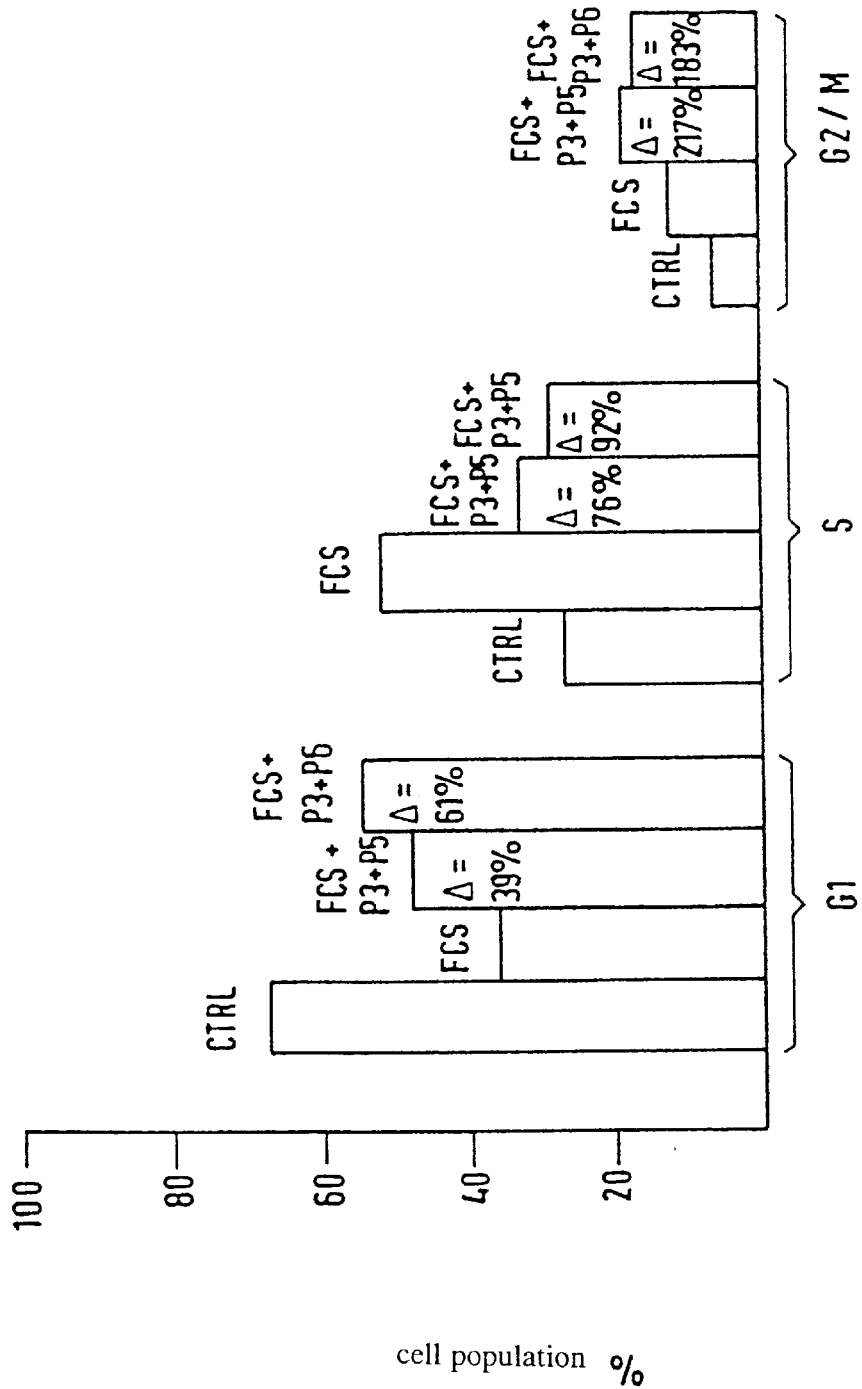

FIG. 5 shows that the combination of the peptides P3 and P5 at a concentration of $10^{-5}$ M each as well as the combination of P3 and P6 at a concentration of $10^{-5}$ M each results in an increase of the G1 phase and the G2/M phase as well as in a decrease of the S phase in MCF-7 cells that have been stimulated by 10% fetal calf serum (FCS). The morphology of the cells treated with these combinations of peptides corresponds to that of apoptotic cells.

Figure 6:
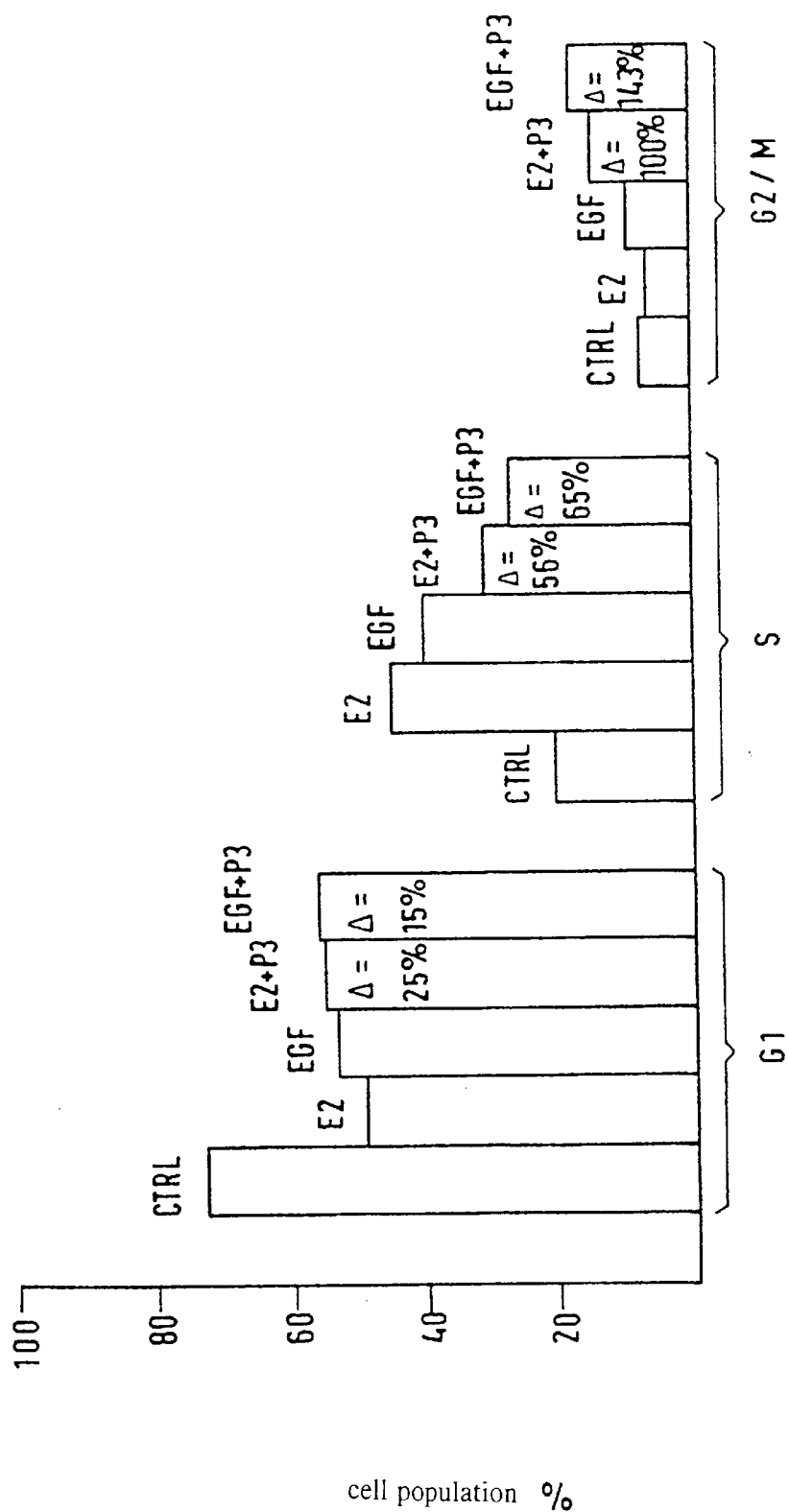

FIG. 6 shows that the peptide P3 of the present invention at a concentration of $10^{-5}$ M increases the G1- and the G2 phases as well as decreases the S phase in MCF-7 cells that have been stimulated by estradiol (E2) at an optimal concentration of $10^{-9}$ M or by epidermal growth factor (EGF) at an optimal concentration of $10^{-8}$ M. The morphology of the cells treated with P3 corresponds to that of apoptotic cells.

Figure 7:
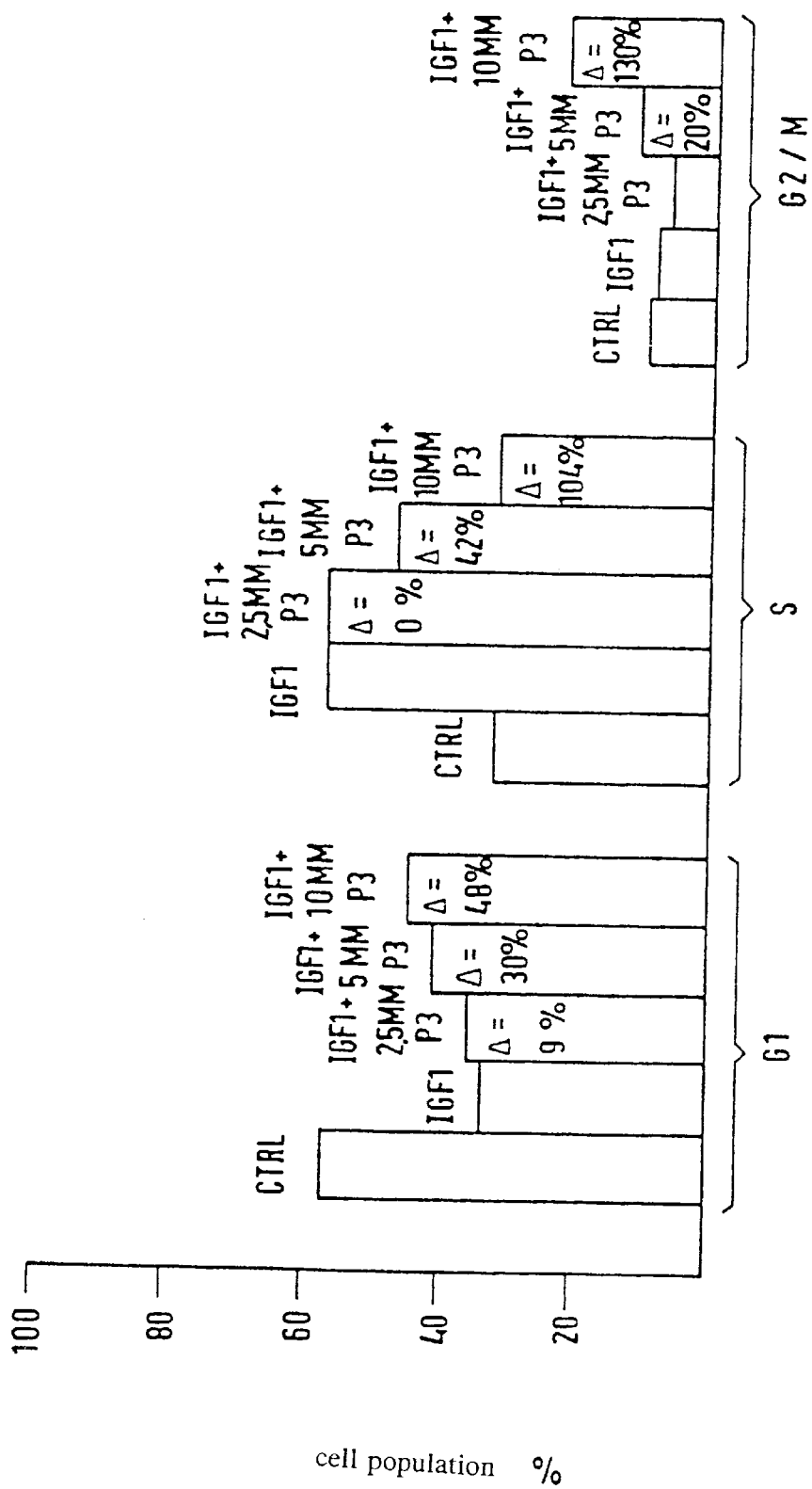

FIG. 7 shows that the peptide P3 of the present invention blocks the progression of the cell cycle that is caused by IGF-1 $[10^{-8}$ M] in a dose-dependent manner. The morphology of the cells treated with P3 $[5 \times 10^{-6}$ M] and in particular of the cells treated with P3 $[10^{-5}$ M] each corresponds to that of apoptotic cells.

Figure 8:
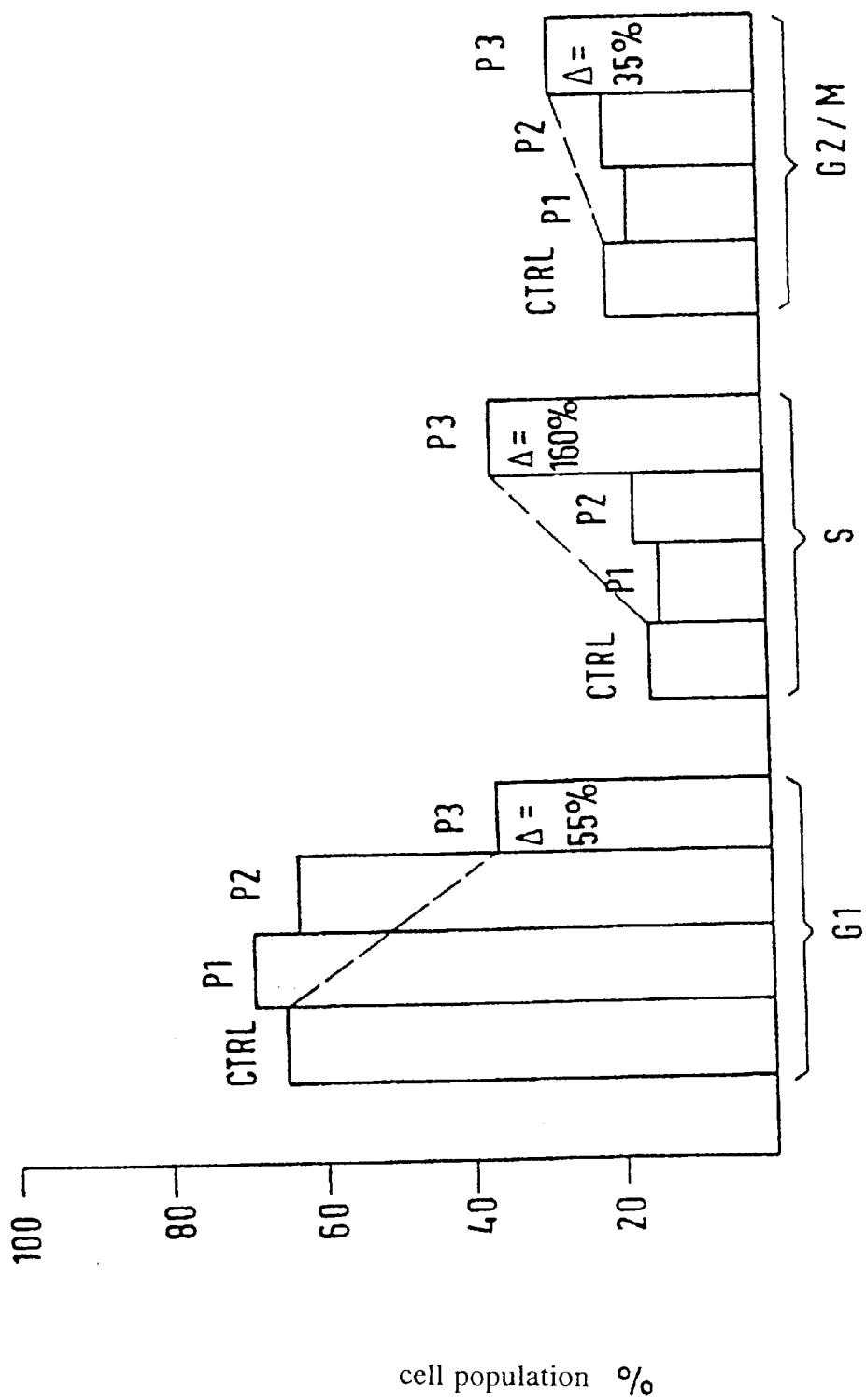

FIG. 8 shows that, under serum-free conditions, the peptide P3 $[10^{-5}$ M] of the present invention reduces the G1 phase and increases the S and G2/M phases in SAOS-2 cells that have been synchronized in the G0/G1 phase. The morphology of the cells treated with P3 corresponds to that of apoptotic cells.

Figure 9:
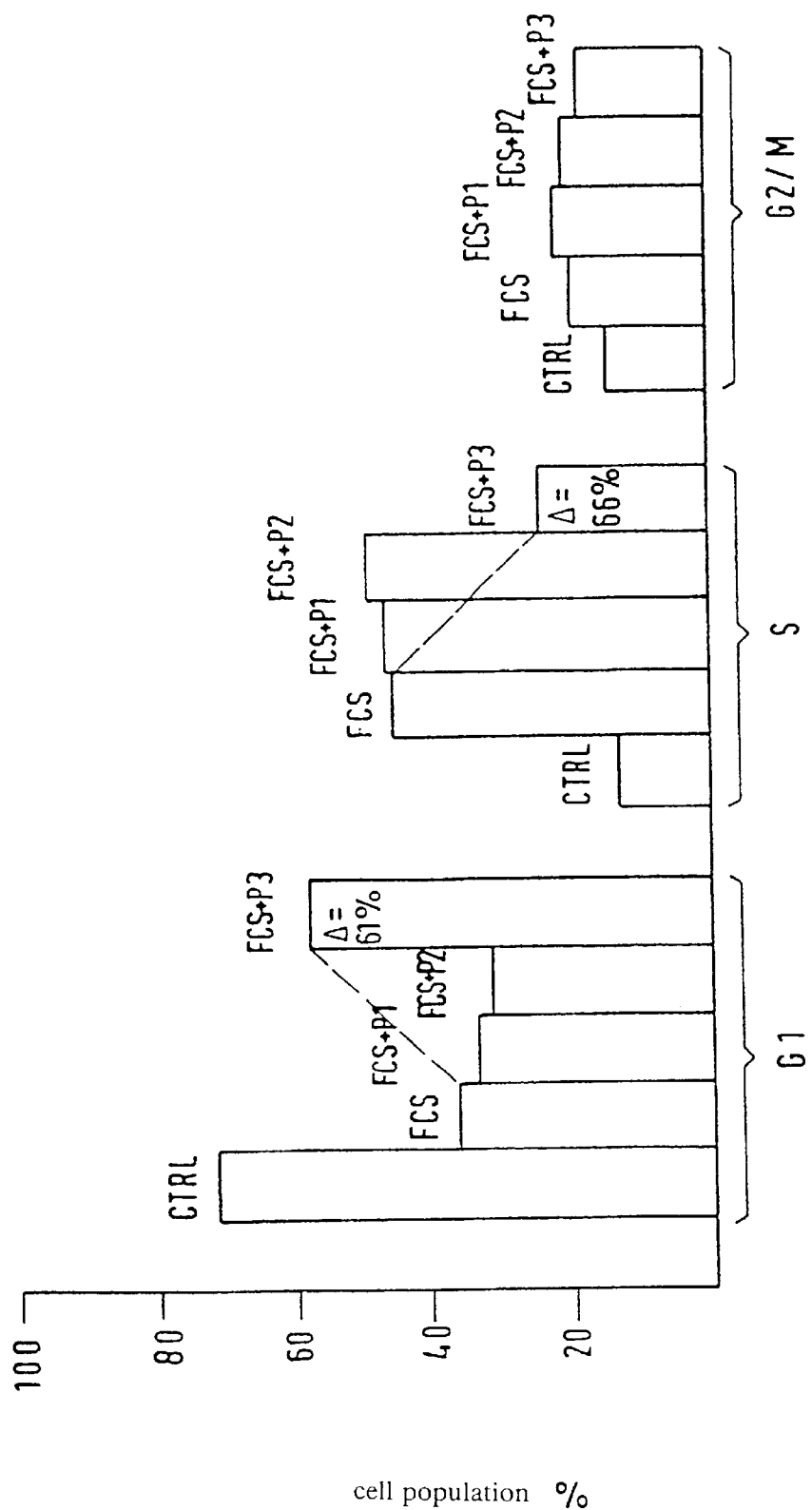

FIG. 9 shows that the peptide P3 $[10^{-5}$ M] increases the G1 phase and decreases the S phase in SAOS-2 cells that have been stimulated by 10% FCS. The morphology of the cells treated with P3 corresponds to that of apoptotic cells.

Figure 10:
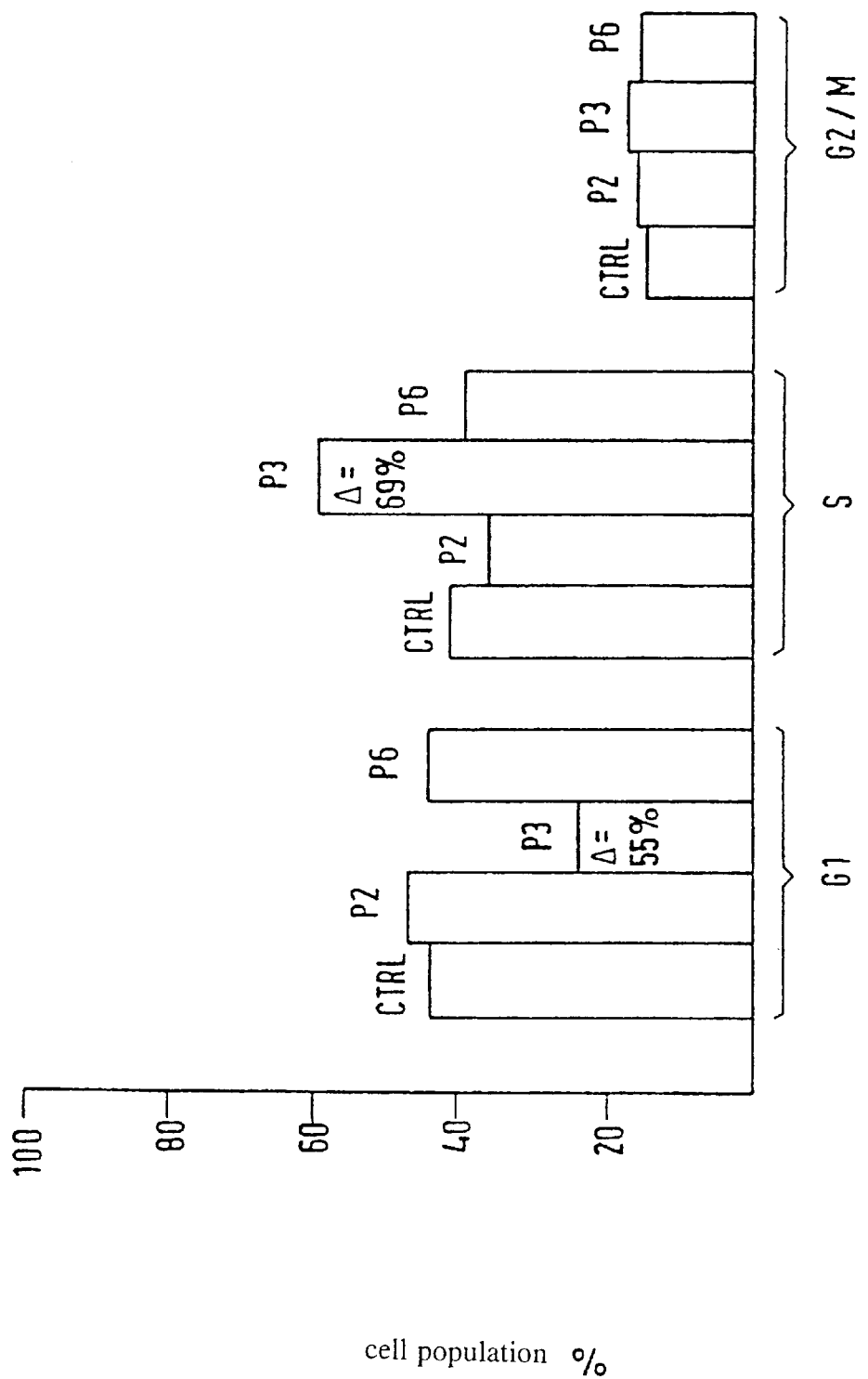

FIG. 10 shows that the peptide P3 $[10^{-5}$ M] according to the present invention reduces the G1 phase and increases the S phase of asynchronously growing MCF-7 cells that have been incubated in DMEM cell culture medium containing 10% FCS. The morphology of said cells treated with P3 corresponds to that of apoptotic cells.

Figure 11:
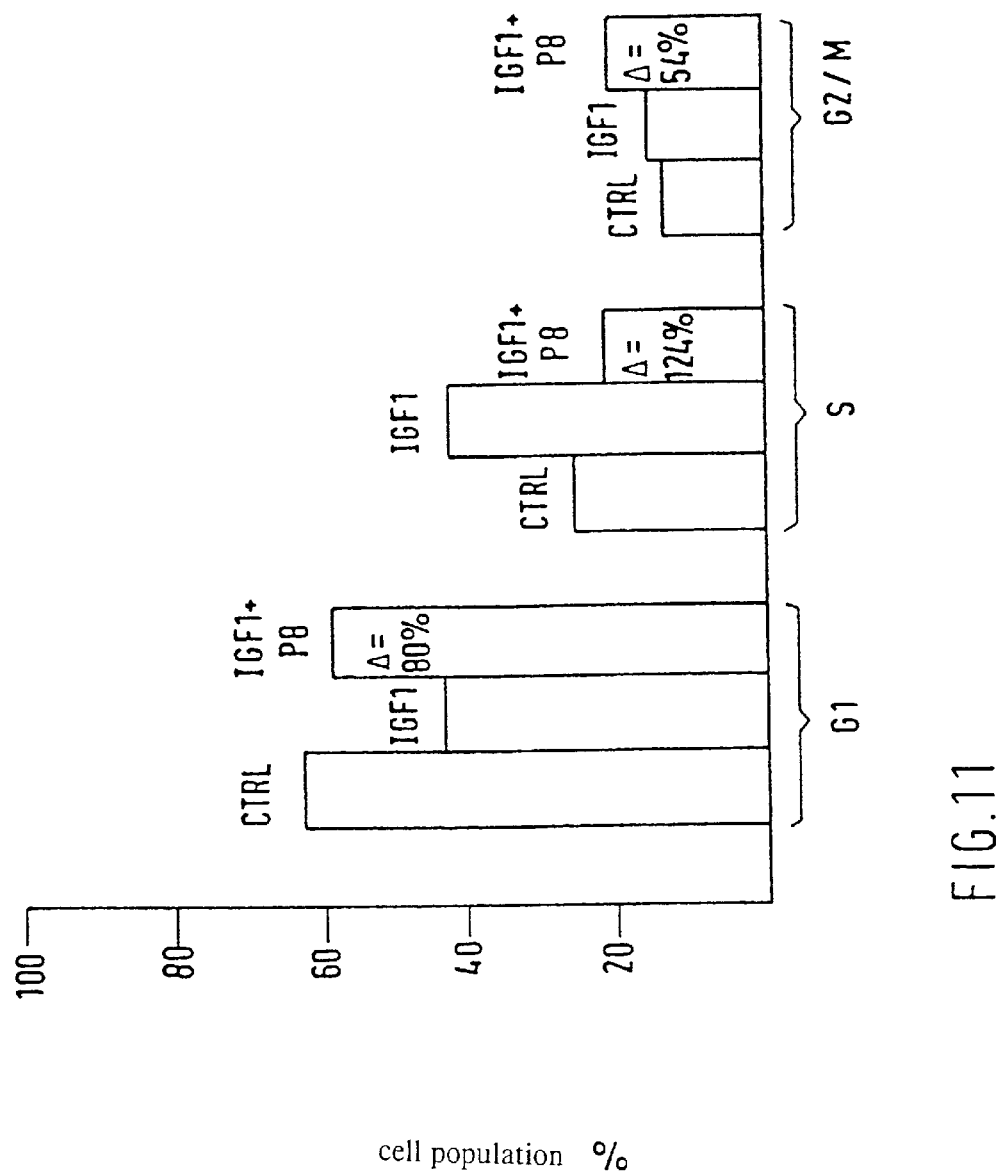

FIG. 11 shows that the peptide P8 $[10^{-5}$ M] of the present invention increases the G1 phase and the G2/M phase as well as decreases the S phase in MCF-7 cells that have been stimulated by IGF-1 at an optimal concentration of $10^{-8}$ M. Accordingly, P8 blocks the effect of IGF-1 on MCF-7 cells. In particular, P8 delays the progression of the cell cycle caused by IGF-1 and thus delays cell division. The morphology of said cells treated with P8 corresponds to that of apoptotic cells.

Figure 12:
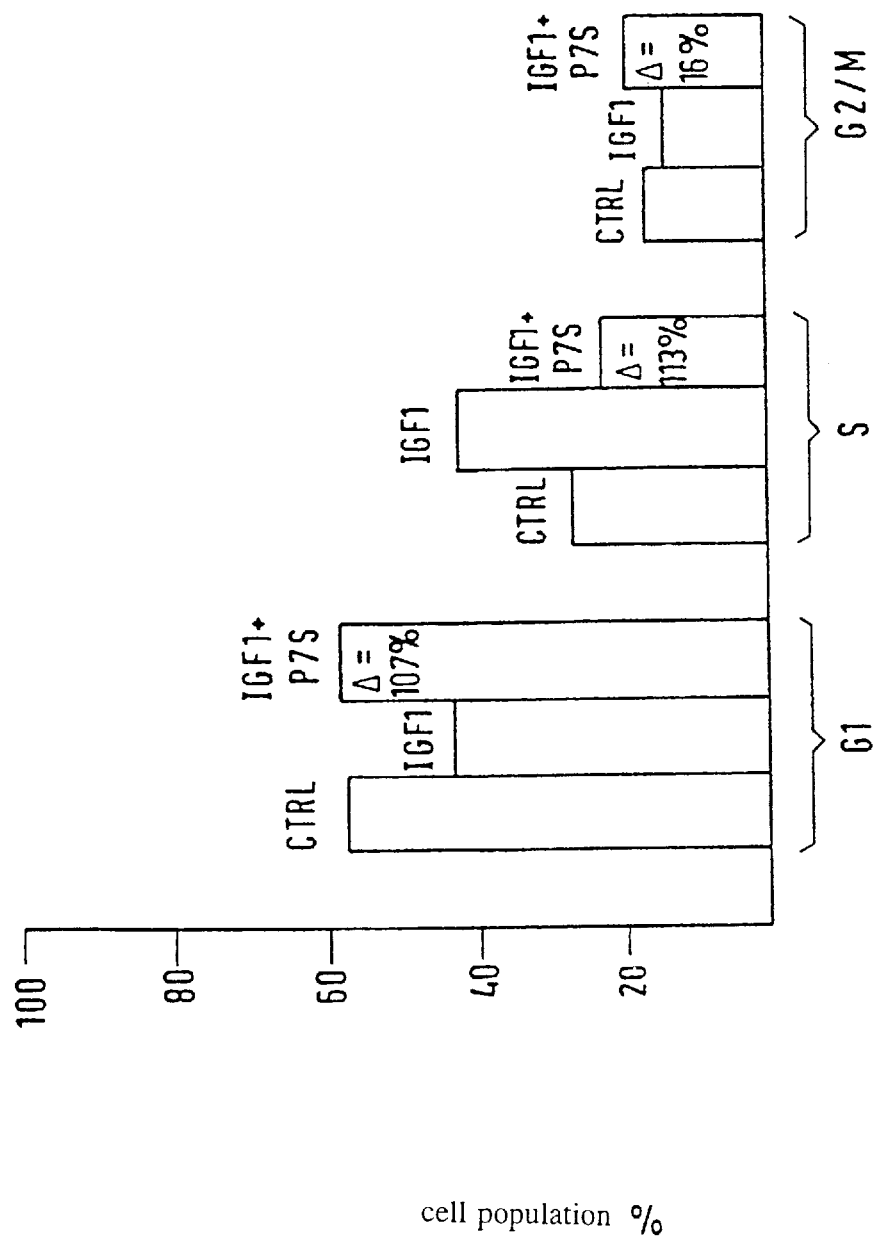

FIG. 12 shows that the peptide P7s $[10^{-5}$ ] of the present invention increases the G1 phase and the G2/M phase as well as decreases the S phase in MCF-7 cells that have been stimulated by IGF-1 at an optimal concentration of $10^{-8}$ M. Accordingly, P7s blocks the effect of IGF-1 on MCF-7 cells. In particular, P7s delays the progression of the cell cycle caused by IGF-1 and thus delays cell division. The morphology of said cells treated with P7s corresponds to that of apoptotic cells.

Figure 13:
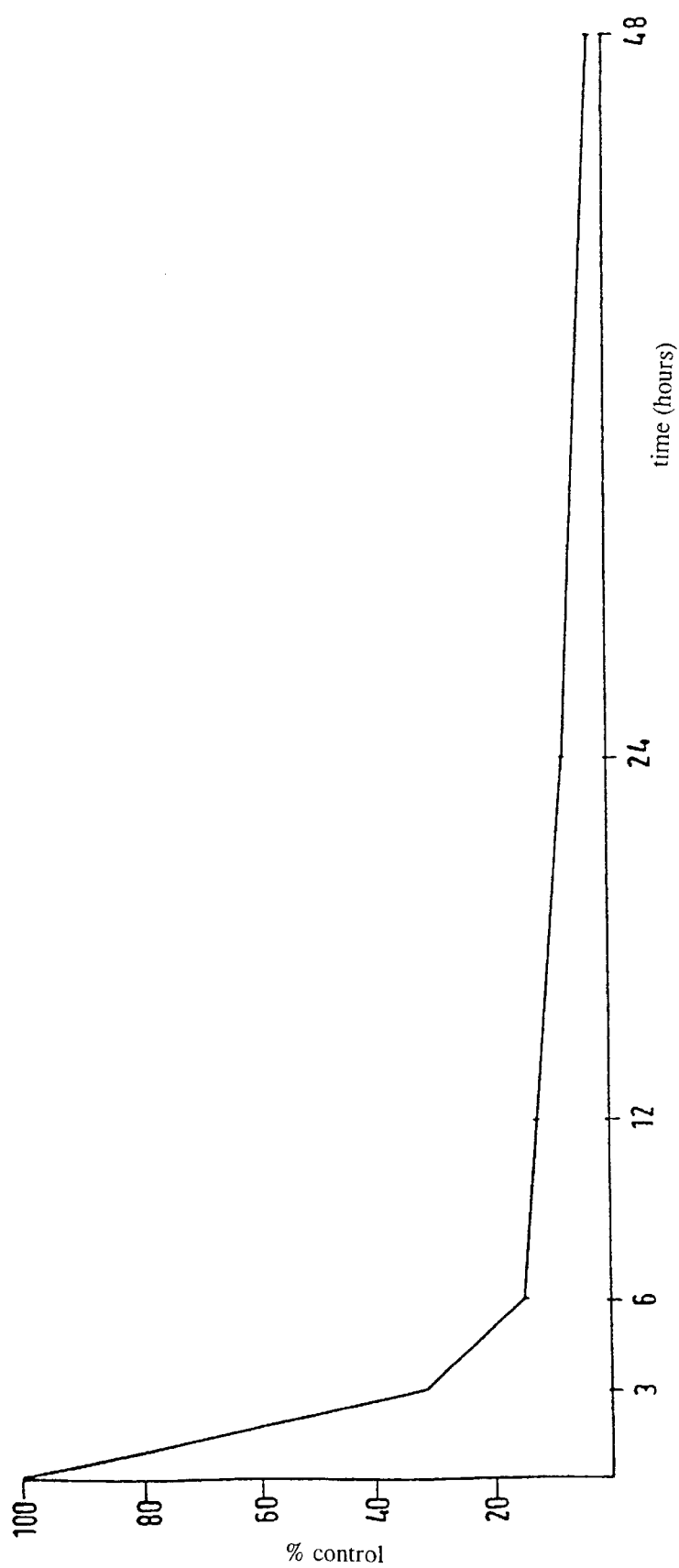
FIG. 13 shows the cytotoxic effect of the peptide P3 on K562 cells.

FIG. 13 shows the cytotoxic effect of the peptide P3 $[10^{-5}$ M] of the present invention on asynchronously growing K562 cells incubated in RPMI cell culture medium to be time-dependent. The results have been plotted as the living cells treated with P3 being a percentage of the living cells not treated with P3. The number of the living cells has been determined by counting at least 200 cells at each time point according to the trypan blue method.

Figure 14:
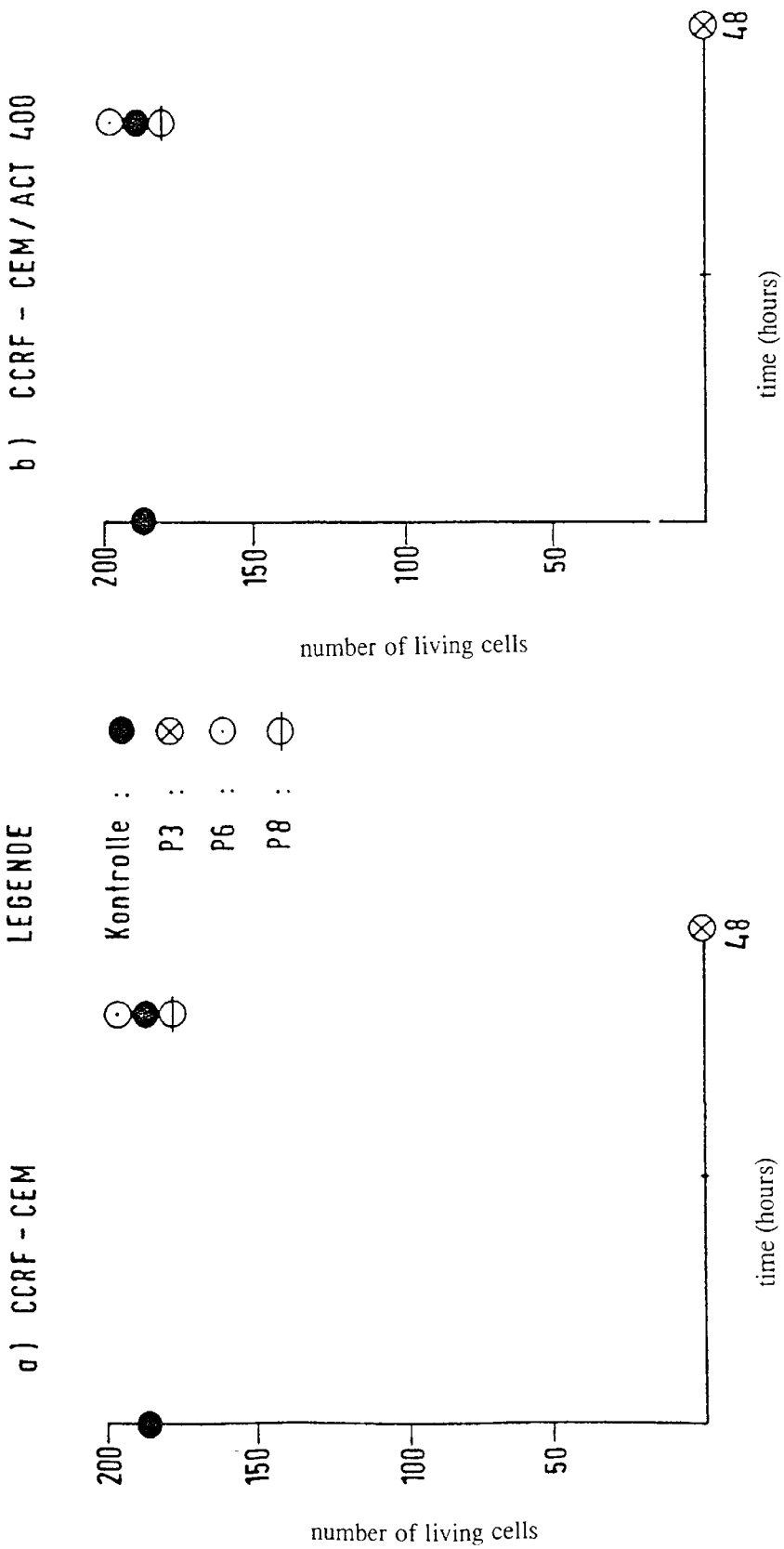
FIG. 14 shows the cytotoxic effect of peptide P3 on CCRF-CEM cells and CCRF-CEM/ACT 400 cells.

FIG. 14($a$ and $b$) shows the peptide according to the present invention P3 $[10^{-5}$ M] to act in a cytotoxic manner on asynchronously growing CCRF-CEM$_{sensitive}$ cells and CCRF-CEM/ACT 400$_{resistant}$ cells that have been incubated in a RPMI culture medium containing 10% FCS.

Figure 15:
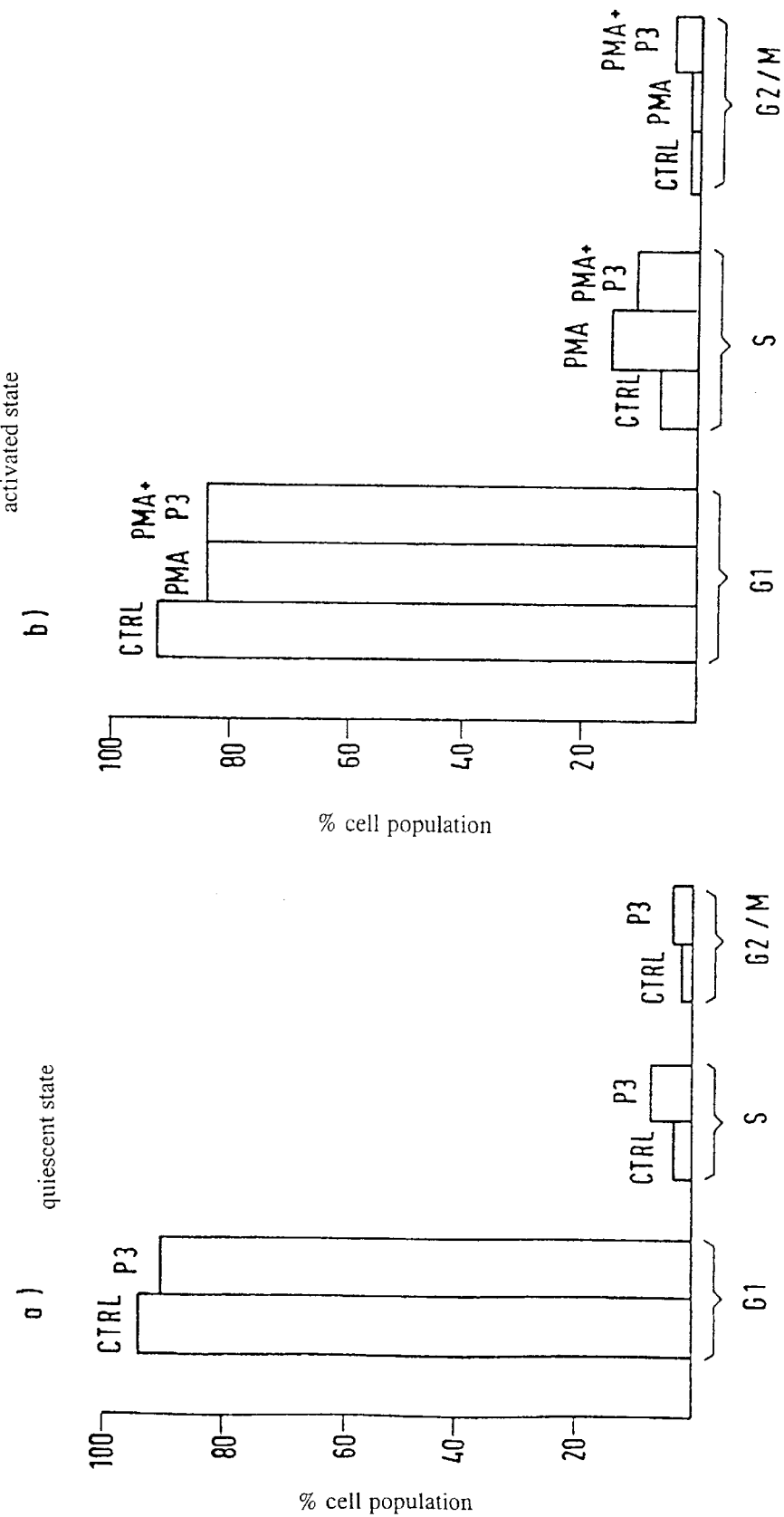
FIG. 15 shows the effect of peptide P3 on normal peripheral blood mononuclear cells.

The FIG. 15($a$ and $b$) shows the peptide P3 of the present invention $[10^{-5}$ M] to have no effect on normal human peripheral blood mononuclear cells, irrespective of whether they are in an quiescent (a) state or in an activated (b) state.

Accordingly, the cells treated with P3 do not show any morphological changes. The incubation of cells with P3 was performed for a time period of 24 hours.

Table 1 shows that the peptides P5 and P6 of the present invention each at a concentration of $10^{-5}$ M reduce the S phase in MCF-7 cells that have been stimulated by IGF-1 $[10^{-8}$ M] or insulin $[10^{-6}$ M], respectively. The peptide Penetratin $[10^{-5}$ M] did not show any effect, as expected.

Table 2 shows that the peptides P5 and P6 of the present invention at a concentration of $5 \times 10^{-5}$ M each results in an increase of the G1 phase and a decrease of the S phase in SAOS-2 cells that have been stimulated by 10% FCS.

Taken together, based on FIGS. 1 to 15 and tables 1 and 2, it may be ascertained that the peptides P3, P5, P6, P7s or P8 of the present invention alone and/or in combination have the property of considerably delaying the progression of the cell cycle and thus the cell division of the MCF-7 breast cancer cells, of the SAOS-2 osteosarcoma cells or of leukemia cells (K562, CCRF-CEM$_{sensitive}$, CCRF-CEM/ACT 400$_{resistant}$) under particular conditions of cell culture. The data shown for IGF-1 $[10^{-8}$ M] also apply to insulin $[10^{-6}$ M].

As a result, these peptides have the potential to also be effective antineoplastic agents against the growth of cancer in vivo in human beings.

The invention is now illustrated by way of the following examples:

EXAMPLES

The experimental setting comprises experiments with the breast cancer cell line MCF-7 containing an intact retinblastoma protein and the human osteosarcoma cell line SAOS-2 containing a defective retinoblastoma protein. Cells are seeded in 12-well plates at 100000 (=one hundred thousand) cells/well/ml in RPMI medium or DMEM medium containing 10% FCS and allowed to adhere for 24 hours. Subsequently, the cells are starved by incubation for 3 days in DMEM without FCS, such that they are synchronized in the G0/G1 phase and then the cells are stimulated by 10% FCS or $10^{-8}$ M IGF-1 or $10^{-6}$ M insulin, respectively, for 24 hours. The effect of each of the added peptides on each of the above modes of stimulation, which effect reflects the rate of cell division, is investigated. The control (cells synchronized in G0/G1) is fixed at time 0 after three days of starvation. The remaining cells (+/−peptide) are fixed after 24 hours. The cells are subsequently analyzed by FACS for their cell cycle distribution. Analogous methods are to be found e.g. in R. Fahraeus et al., Current Biology, 1996, vol. 6, no. 1, pp. 84–91 and L. Zhu et al., Genes & Development, 1993, vol. 7, pp. 1111–1125.

The second experimental setting relates to the leukemia cell lines K562 and CCRF-CEM and CCRF-CEM/ACT400. 100000 asynchronously growing cells/well/ml RPMI/10% FCS have each been incubated for 48 hours with each of the peptides in 6-well plates. As a readout, the number of dead cells/200 counted cells is determined according to the trypan blue method (L. D. Attardi et al., The EMBO Journal, 1996, vol. 15, no. 14, pp. 3693–3701 and M. K. Reeder & H. C. Isom, Cell Growth & Differentiation 196, vol. 7, pp. 449–460) after this 48-hour incubation. The more dead cells, the more cytotoxic the peptide and thus the more effective the peptide.

The results of the examples are illustrated in the FIGS. 1 to 15 and in the tables 1 and 2.

TABLE 1

TAB. 1/2

|     | Control | IGF-I | P5 + IGF-I | P6 + IGF-I | Penetratin + IGF-I |
|-----|---------|-------|------------|------------|--------------------|
| G1: | 70.2    | 47.3  | 54.0       | 53.7       | 50.5               |
| S:  | 17.7    | 45.4  | 32.4       | 27.7       | 39.3               |
| G2/M:| 12.1   | 7.3   | 13.6       | 18.6       | 10.1               |

|     | Control | Insulin | P6 + Insulin | Penetratin + Insulin |
|-----|---------|---------|--------------|----------------------|
| G1: | 70.2    | 38.3    | 48.7         | 39.6                 |
| S:  | 17.7    | 52.8    | 36.6         | 49.6                 |
| G2/M:| 12.1   | 8.9     | 14.6         | 10.9                 |

TABLE 2

TAB. 2/2

|     | Control | FCS  | P5 + FCS | P6 + FCS | Penetratin + FCS |
|-----|---------|------|----------|----------|------------------|
| G1: | 79.6    | 63.1 | 73.5     | 76.6     | 62.3             |
| S:  | 12.0    | 32.5 | 13.2     | 12.2     | 29.9             |
| G2/M:| 8.4    | 4.4  | 13.3     | 11.2     | 7.8              |

What is claimed is:

1. An antiproliferative peptide AB or BA consisting of:
   an antiproliferative component (A) that is a fragment of a tumor suppressor protein or a peptide sequence hydropathically homologous thereto having the property of binding to a growth factor segment or to a growth factor receptor segment, and
   a component (B) that protects component (A) from the proteolytic degradation by proteases, and that is a nuclear localization sequence (NLS) selected from the group consisting of
   a) the amino acid sequence PKKKRKV (SEQ. ID. No. 21),
   b) the amino acid sequence RQIKIWFQNRRMKWKK (SEQ. ID. No. 22),
   c) a bipartite nuclear localization sequence ("NLS"), and
   d) the RNP A1 NLS;
   wherein the antiproliferative peptide is cytotoxic to tumor cells.

2. The peptide according to claim 1, wherein component (A) is hydropathically complementary to a growth factor segment or a growth factor receptor segment.

3. The peptide according to claim 1, wherein component (A) is a tumor suppressor protein fragment of the retinoblastoma protein (RB1).

4. The peptide according to claim 1, wherein component (A) is the amino acid sequence FYKK (SEQ. ID. No. 23), or an amino acid sequence that is hydropathically homologous thereto in at least two positions.

5. The peptide according to claim 1, wherein component (A) is the amino acid sequence LFYKKV (SEQ. ID. No. 4), or an amino acid sequence that is hydropathically homologous thereto in at least two positions.

6. The peptide according to claim 1, wherein the growth factor segment or the growth factor receptor segment comprises an amino acid sequence with the hydropathic profile:
   hydrophobic amino acid -X-hydrophobic amino acid -X-hydrophilic amino acid, wherein X represents any amino acid.

7. The peptide according to claim 2, wherein the growth factor segment or the growth factor receptor segment comprises an amino acid sequence corresponding to LXCXE (SEQ. ID. No. 1), or an amino acid sequence corresponding to FVCGD (SEQ. ID. No. 3), wherein X represents any amino acid.

8. The peptide according to claim 7, wherein the amino acid sequence LXCXE (SEQ. ID. No. 1) is derived from insulin.

9. The peptide according to claim 1 wherein the peptide is selected from the group consisting of:
   a) LFYKKVPKKKRKV (SEQ. ID. No. 10);
   b) LFYKKVPKKKRKV (SEQ. ID. No. 10), wherein all the amino acids are in the D form;
   c) LFYKKVRQIKIWFQNRRMKWKK (SEQ. ID. No. 11); and
   d) LFYKKVRQIKIWFQNRRMKWKK (SEQ. ID. No. 11), wherein all the amino acids are in the D form.

10. A pharmaceutical composition containing one or more peptides according to claim 1.

11. The pharmaceutical composition according to claim 10, in the form of ointments, solutions, dispersions, emulsions, aerosols, foams, particles, pills, pastilles, tablets, dragées or capsules.

12. The pharmaceutical composition according to claim 10, wherein the particles are selected from the group consisting of granules, agglomerates, powders, micropearls, and adsorbates.

13. A composition comprising:
    one or more peptides according to claim 1 and a carrier.

14. The peptide according to claim 1 wherein the peptide is selected from the group consisting of:
    a) KVLYFKRQIKIWFQNRRMKWKK (SEQ. ID. No. 5); and
    b) KVLYFKRQIKIWFQNRRMKWKK (SEQ. ID. No. 5), wherein all the amino acids are in the D form.

* * * * *

```
                    SEQUENCE LISTING

<160> NUMBER OF SEQ ID NOS: 23

<210> SEQ ID NO 1
<211> LENGTH: 5
<212> TYPE: PRT
<213> ORGANISM: Homo sapiens
<220> FEATURE:
<221> NAME/KEY: UNSURE
<222> LOCATION: (1)..(5)
<223> OTHER INFORMATION: Where all amino acids may be in L or D
      configuration
<221> NAME/KEY: UNSURE
<222> LOCATION: (2)
<223> OTHER INFORMATION: Where Xaa at position 2 may be any amino acid
<221> NAME/KEY: UNSURE
<222> LOCATION: (4)
<223> OTHER INFORMATION: Where Xaa at position 4 may be any amino acid

<400> SEQUENCE: 1

Leu Xaa Cys Xaa Glu
 1               5

<210> SEQ ID NO 2
<211> LENGTH: 5
<212> TYPE: PRT
<213> ORGANISM: Homo sapiens
<220> FEATURE:
<221> NAME/KEY: UNSURE
<222> LOCATION: (1)..(5)
<223> OTHER INFORMATION: Where all amino acids may be in L or D
      configuration

<400> SEQUENCE: 2

Leu Val Cys Gly Glu
 1               5

<210> SEQ ID NO 3
<211> LENGTH: 5
<212> TYPE: PRT
<213> ORGANISM: Homo sapiens
<220> FEATURE:
<221> NAME/KEY: UNSURE
<222> LOCATION: (1)..(5)
<223> OTHER INFORMATION: Where all amino acids may be in L or D
      configuration

<400> SEQUENCE: 3
```

Phe Val Cys Gly Asp
1               5

<210> SEQ ID NO 4
<211> LENGTH: 6
<212> TYPE: PRT
<213> ORGANISM: Homo sapiens
<220> FEATURE:
<221> NAME/KEY: UNSURE
<222> LOCATION: (1)..(6)
<223> OTHER INFORMATION: Where all amino acids may be in L or D
      configuration

<400> SEQUENCE: 4

Leu Phe Tyr Lys Lys Val
1               5

<210> SEQ ID NO 5
<211> LENGTH: 22
<212> TYPE: PRT
<213> ORGANISM: Artificial Sequence
<220> FEATURE:
<223> OTHER INFORMATION: Description of Artificial Sequence: Peptide
<221> NAME/KEY: UNSURE
<222> LOCATION: (1)..(22)
<223> OTHER INFORMATION: Where all amino acids may be in L or D
      configuration

<400> SEQUENCE: 5

Lys Val Leu Tyr Phe Lys Arg Gln Ile Lys Ile Trp Phe Gln Asn Arg
1               5                   10                  15

Arg Met Lys Trp Lys Lys
            20

<210> SEQ ID NO 6
<211> LENGTH: 44
<212> TYPE: PRT
<213> ORGANISM: Artificial Sequence
<220> FEATURE:
<223> OTHER INFORMATION: Description of Artificial Sequence: Peptide
<221> NAME/KEY: UNSURE
<222> LOCATION: (1)..(44)
<223> OTHER INFORMATION: Where all amino acids may be in L or D
      configuration

<400> SEQUENCE: 6

Leu Phe Tyr Lys Lys Val Gly Gly Gly Leu Phe Tyr Lys Lys Val Gly
1               5                   10                  15

Gly Gly Leu Phe Tyr Lys Lys Val Gly Gly Gly Leu Phe Tyr Lys Lys
            20                  25                  30

Val Gly Gly Gly Lys Arg Gly Lys Arg Gly Lys Gly
            35                  40

<210> SEQ ID NO 7
<211> LENGTH: 20
<212> TYPE: PRT
<213> ORGANISM: Artificial Sequence
<220> FEATURE:
<223> OTHER INFORMATION: Description of Artificial Sequence: Peptide
<221> NAME/KEY: UNSURE
<222> LOCATION: (1)..(20)
<223> OTHER INFORMATION: Where all amino acids may be in L or D
      configuration

<400> SEQUENCE: 7

Gly Gly Gly Gly Gly Gly Gly Gly Gly Gly Gly Lys Arg Gly Lys
1               5                   10                  15

Arg Gly Lys Gly
              20

<210> SEQ ID NO 8
<211> LENGTH: 40
<212> TYPE: PRT
<213> ORGANISM: Artificial Sequence
<220> FEATURE:
<223> OTHER INFORMATION: Description of Artificial Sequence: Peptide
<221> NAME/KEY: UNSURE
<222> LOCATION: (1)..(40)
<223> OTHER INFORMATION: Where all amino acids may be in L or D
      configuration

<400> SEQUENCE: 8

Leu Phe Tyr Lys Lys Val Gly Gly Gly Leu Phe Tyr Lys Lys Val Gly
 1               5                  10                  15

Gly Gly Leu Phe Tyr Lys Lys Val Gly Gly Gly Leu Phe Tyr Lys Lys
            20                  25                  30

Val Gly Gly Gly Lys Lys Lys Gly
        35                  40

<210> SEQ ID NO 9
<211> LENGTH: 16
<212> TYPE: PRT
<213> ORGANISM: Artificial Sequence
<220> FEATURE:
<223> OTHER INFORMATION: Description of Artificial Sequence: Peptide
<221> NAME/KEY: UNSURE
<222> LOCATION: (1)..(16)
<223> OTHER INFORMATION: Where all amino acids may be in L or D
      configuration

<400> SEQUENCE: 9

Gly Gly Gly Gly Gly Gly Gly Gly Gly Gly Gly Gly Lys Lys Lys Gly
 1               5                  10                  15

<210> SEQ ID NO 10
<211> LENGTH: 13
<212> TYPE: PRT
<213> ORGANISM: Artificial Sequence
<220> FEATURE:
<223> OTHER INFORMATION: Description of Artificial Sequence: Peptide
<221> NAME/KEY: UNSURE
<222> LOCATION: (1)..(13)
<223> OTHER INFORMATION: Where all amino acids may be in L or D
      configuration

<400> SEQUENCE: 10

Leu Phe Tyr Lys Lys Val Pro Lys Lys Lys Arg Lys Val
 1               5                  10

<210> SEQ ID NO 11
<211> LENGTH: 22
<212> TYPE: PRT
<213> ORGANISM: Artificial Sequence
<220> FEATURE:
<223> OTHER INFORMATION: Description of Artificial Sequence: Peptide
<221> NAME/KEY: UNSURE
<222> LOCATION: (1)..(22)
<223> OTHER INFORMATION: Where all amino acids may be in L or D
      configuration

<400> SEQUENCE: 11

Leu Phe Tyr Lys Lys Val Arg Gln Ile Lys Ile Trp Phe Gln Asn Arg
 1               5                  10                  15

Arg Met Lys Trp Lys Lys

<210> SEQ ID NO 12
<211> LENGTH: 44
<212> TYPE: PRT
<213> ORGANISM: Artificial Sequence
<220> FEATURE:
<223> OTHER INFORMATION: Description of Artificial Sequence: Peptide
<221> NAME/KEY: UNSURE
<222> LOCATION: (1)..(44)
<223> OTHER INFORMATION: Where all amino acids may be in L or D
      configuration

<400> SEQUENCE: 12

Lys Val Leu Tyr Phe Lys Gly Gly Gly Lys Val Leu Tyr Phe Lys Gly
 1               5                  10                  15

Gly Gly Lys Val Leu Tyr Phe Lys Gly Gly Gly Lys Val Leu Tyr Phe
            20                  25                  30

Lys Gly Gly Gly Lys Arg Gly Lys Arg Gly Lys Gly
        35                  40

<210> SEQ ID NO 13
<211> LENGTH: 6
<212> TYPE: PRT
<213> ORGANISM: Artificial Sequence
<220> FEATURE:
<223> OTHER INFORMATION: Description of Artificial Sequence: Peptide
<221> NAME/KEY: UNSURE
<222> LOCATION: (1)..(6)
<223> OTHER INFORMATION: Where all amino acids may be in L or D
      configuration

<400> SEQUENCE: 13

Lys Val Leu Tyr Phe Lys
 1               5

<210> SEQ ID NO 14
<211> LENGTH: 40
<212> TYPE: PRT
<213> ORGANISM: Artificial Sequence
<220> FEATURE:
<223> OTHER INFORMATION: Description of Artificial Sequence: Peptide
<221> NAME/KEY: UNSURE
<222> LOCATION: (1)..(40)
<223> OTHER INFORMATION: Where all amino acids may be in L or D
      configuration

<400> SEQUENCE: 14

Lys Val Leu Tyr Phe Lys Gly Gly Gly Lys Val Leu Tyr Phe Lys Gly
 1               5                  10                  15

Gly Gly Lys Val Leu Tyr Phe Lys Gly Gly Gly Lys Val Leu Tyr Phe
            20                  25                  30

Lys Gly Gly Gly Lys Lys Lys Gly
        35                  40

<210> SEQ ID NO 15
<211> LENGTH: 18
<212> TYPE: RNA
<213> ORGANISM: Artificial Sequence
<220> FEATURE:
<223> OTHER INFORMATION: Description of Artificial Sequence: mRNA
<221> NAME/KEY: mRNA
<222> LOCATION: (1)..(18)
<223> OTHER INFORMATION: mRNA

<400> SEQUENCE: 15
cuuuucuaca agaagguu                                              18

```
<210> SEQ ID NO 16
<211> LENGTH: 39
<212> TYPE: RNA
<213> ORGANISM: Artificial Sequence
<220> FEATURE:
<223> OTHER INFORMATION: Description of Artificial Sequence:  mRNA
<221> NAME/KEY: mRNA
<222> LOCATION: (1)..(39)
<223> OTHER INFORMATION: mRNA

<400> SEQUENCE: 16
cuuuucuaca agaagguucc uagaagaag cguaagguu                              39

<210> SEQ ID NO 17
<211> LENGTH: 66
<212> TYPE: RNA
<213> ORGANISM: Artificial Sequence
<220> FEATURE:
<223> OTHER INFORMATION: Description of Artificial Sequence:  mRNA
<221> NAME/KEY: mRNA
<222> LOCATION: (1)..(66)
<223> OTHER INFORMATION: mRNA

<400> SEQUENCE: 17
cuuuucuaca agaagguucg ucaaauaaag auaugguucc aaaaucgucg uaugaagugg      60
aagaag                                                                66

<210> SEQ ID NO 18
<211> LENGTH: 66
<212> TYPE: RNA
<213> ORGANISM: Artificial Sequence
<220> FEATURE:
<223> OTHER INFORMATION: Description of Artificial Sequence:  mRNA
<221> NAME/KEY: mRNA
<222> LOCATION: (1)..(66)
<223> OTHER INFORMATION: mRNA

<400> SEQUENCE: 18
aagguucuuu acuucaagcg ucaaauaaag auaugguucc aaaaucgucg uaugaagugg      60
aagaag                                                                66

<210> SEQ ID NO 19
<211> LENGTH: 5
<212> TYPE: PRT
<213> ORGANISM: Artificial Sequence
<220> FEATURE:
<223> OTHER INFORMATION: Description of Artificial Sequence:  Peptide
<221> NAME/KEY: PEPTIDE
<222> LOCATION: (1)..(5)
<223> OTHER INFORMATION: Peptide

<400> SEQUENCE: 19

Arg Glu Gly Ser Asn
  1               5

<210> SEQ ID NO 20
<211> LENGTH: 5
<212> TYPE: PRT
<213> ORGANISM: Artificial Sequence
<220> FEATURE:
<223> OTHER INFORMATION: Description of Artificial Sequence:  Peptide
<221> NAME/KEY: PEPTIDE
<222> LOCATION: (1)..(5)
<223> OTHER INFORMATION: Peptide

<400> SEQUENCE: 20
```

```
Ile Gly Thr Leu Ser
 1               5

<210> SEQ ID NO 21
<211> LENGTH: 7
<212> TYPE: PRT
<213> ORGANISM: Artificial Sequence
<220> FEATURE:
<223> OTHER INFORMATION: Description of Artificial Sequence:  Peptide
<221> NAME/KEY: PEPTIDE
<222> LOCATION: (1)..(7)
<223> OTHER INFORMATION: Peptide

<400> SEQUENCE: 21

Pro Lys Lys Lys Arg Lys Val
 1               5

<210> SEQ ID NO 22
<211> LENGTH: 16
<212> TYPE: PRT
<213> ORGANISM: Artificial Sequence
<220> FEATURE:
<223> OTHER INFORMATION: Description of Artificial Sequence:  Peptide
<221> NAME/KEY: PEPTIDE
<222> LOCATION: (1)..(16)
<223> OTHER INFORMATION: Peptide

<400> SEQUENCE: 22

Arg Gln Ile Lys Ile Trp Phe Gln Asn Arg Arg Met Lys Trp Lys Lys
 1               5                   10                  15

<210> SEQ ID NO 23
<211> LENGTH: 4
<212> TYPE: PRT
<213> ORGANISM: Artificial Sequence
<220> FEATURE:
<223> OTHER INFORMATION: Description of Artificial Sequence:  Peptide
<221> NAME/KEY: PEPTIDE
<222> LOCATION: (1)..(4)
<223> OTHER INFORMATION: Peptide

<400> SEQUENCE: 23

Phe Tyr Lys Lys
 1
```